United States Patent [19]
Reed

[11] Patent Number: 5,740,554
[45] Date of Patent: Apr. 21, 1998

[54] DEVICE FOR SANITARY TAMPON REMOVAL AND DISPOSAL

[76] Inventor: B. Bernetiae Reed, 2711 McConnell Rd., Greensboro, N.C. 27401

[21] Appl. No.: 848,142

[22] Filed: Apr. 28, 1997

Related U.S. Application Data

[63] Continuation-in-part of Ser. No. 573,957, Dec. 15, 1995, abandoned.

[51] Int. Cl.$^6$ .................................................. A41D 19/00
[52] U.S. Cl. .................................... 2/158; 2/159; 2/160
[58] Field of Search ................................. 2/16, 20, 158, 2/159, 160, 161.6, 161.7, 161.8, 163, 168; 206/438, 440, 282, 205, 823; 294/1.3, 1.5, 25; 604/358, 393, 904

[56] References Cited

U.S. PATENT DOCUMENTS

| | | | |
|---|---|---|---|
| 2,380,633 | 7/1945 | Daiber | 2/158 |
| 2,643,388 | 6/1953 | Curtis | 2/158 |
| 2,735,108 | 2/1956 | Cremer | 2/158 |
| 2,773,264 | 12/1956 | Nover | 2/159 |
| 2,976,540 | 3/1961 | Sutherland | 2/161 |
| 4,017,907 | 4/1977 | Margolis | 2/153 |
| 4,245,656 | 1/1981 | Farr et al. | 2/160 |
| 4,253,660 | 3/1981 | Tiktin | 2/160 |
| 4,534,066 | 8/1985 | Hansson | 2/159 |
| 4,645,251 | 2/1987 | Jacobs | 294/1.3 |
| 4,677,697 | 7/1987 | Hayes | 2/159 |
| 4,768,818 | 9/1988 | Kolic | 294/1.3 |
| 4,788,733 | 12/1988 | Lerner | 2/159 |
| 4,845,781 | 7/1989 | Strickland | 2/161 |
| 4,902,283 | 2/1990 | Rojko et al. | 604/290 |
| 4,937,881 | 7/1990 | Heise | 2/16 |
| 4,964,188 | 10/1990 | Olson | 2/160 |
| 5,020,159 | 6/1991 | Hellickson | 2/158 |
| 5,020,160 | 6/1991 | Cano | 2/159 |
| 5,149,159 | 9/1992 | Bardes | 294/1.3 |
| 5,186,322 | 2/1993 | Harreld et al. | 2/159 |
| 5,196,244 | 3/1993 | Beck | 2/158 |
| 5,210,880 | 5/1993 | Yale | 2/159 |
| 5,261,531 | 11/1993 | Nieves | 206/205 |
| 5,301,806 | 4/1994 | Olson | 206/273 |
| 5,345,611 | 9/1994 | Smith, Jr. | 2/160 |
| 5,438,708 | 8/1995 | Jacovitz | 2/161.6 |

FOREIGN PATENT DOCUMENTS

| | | |
|---|---|---|
| 2295-885 | 8/1976 | France . |
| 4-215952 | 6/1992 | Japan . |

*Primary Examiner*—Amy B. Vanatta
*Attorney, Agent, or Firm*—Olive & Olive, P.A.

[57] ABSTRACT

This invention comprises a mitten device for sanitarily removing a tampon from a body cavity of an individual and thereafter disposing of the tampon through the solid waste system as opposed to the plumbing system. The mitten is adapted to fit over a hand and wrist and has a front side and a back side. The mitten has an unitary finger portion, a partially detached index finger portion, a thumb portion, a mid-section, a cuff portion, an absorbent pad affixed to the mid-section on the front side of the mitten, and an adhesive tab. The unitary finger portion includes a grasping portion on the front side of the middle finger near the fingertip. In use the mitten is utilized to remove the tampon for disposal from an individual's body. The individual then makes a fist around the tampon. The mitten is then inverted and rolled, and secured with the adhesive tab, thereby encasing the tampon within the mitten for sanitary, compact disposal.

4 Claims, 3 Drawing Sheets

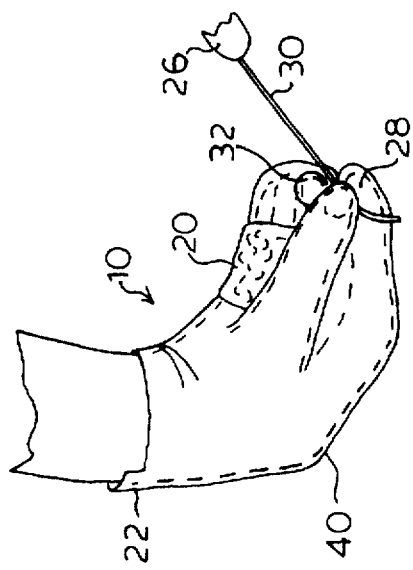
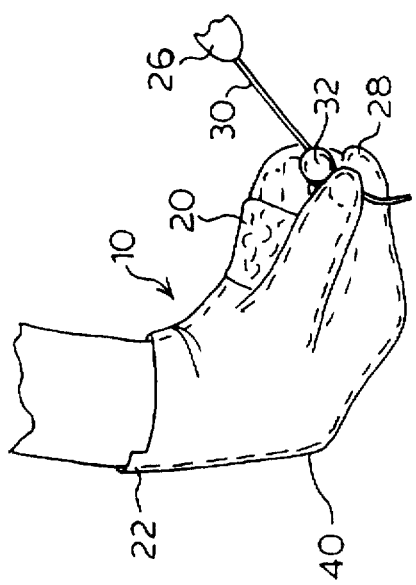
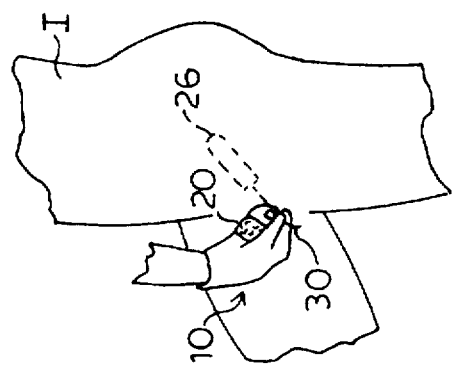
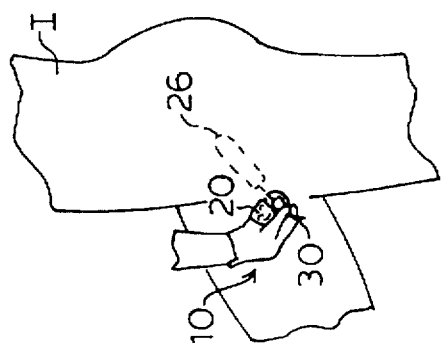
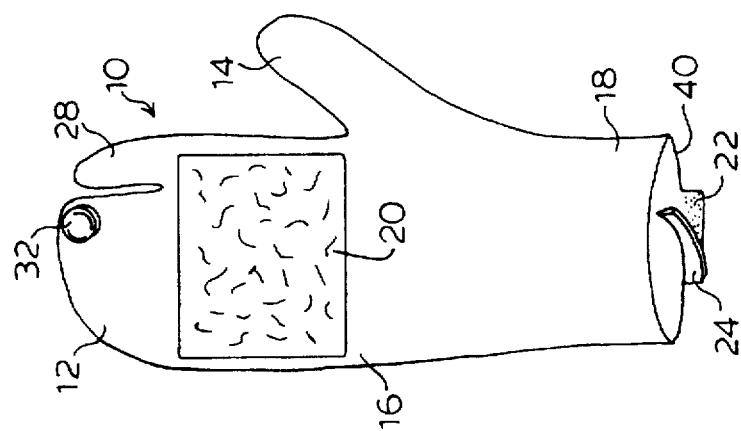

DEVICE FOR SANITARY TAMPON REMOVAL AND DISPOSAL

RELATION TO CO-PENDING APPLICATION

This application is a continuation in part of pending patent application Ser. No. 8/573,957 now abandoned, filed Dec. 15, 1995 entitled "Device and Method for Sanitary Tampon Disposal."

BACKGROUND OF THE INVENTION

1. Field of the Invention

This invention relates to a device for use by an individual to remove a tampon from the individual's body and dispose of the tampon in an effective and sanitary manner.

2. Description of the Related Art

A need exists for a device for use by an individual to remove a tampon in a sanitary manner. Additionally, a need exists for a device for use by an individual which provides for tampon disposal through a solid waste system as opposed to utilizing a plumbing system. Traditional methods of tampon disposal through the solid waste system tend to be less hygienic than utilizing the plumbing system, due to the individual's increased exposure to the used tampon. Tampon disposal through the plumbing system can strain a plumbing system, and can ultimately cause blockages and require reaming of the plumbing system. To accomplish sanitary tampon removal and then disposal within the solid waste system, therefore, a preferred device must prevent soiling the individual during removal from the body, and provide for compact and hygienic temporary storage of the tampon prior to such disposal.

It is well known in the art to provide gloves for protecting an individual's hands under potentially unsanitary conditions. Such devices include surgical gloves, or examination gloves of the type described in U.S. Pat. No. 2,976,540 of Sutherland, which provides a physician's examination hand mitt.

Numerous devices exist which are intended to be worn on an individual's hands and used for sanitarily disposing of waste without soiling the hands. Examples of such devices include: U.S. Pat. No. 4,017,907 of Margolis entitled "Sanitary Hand Covering with Shaping Fasteners;" U.S. Pat. No. 4,645,251 of Jacobs entitled "Glove-Like Waste Disposal System;" U.S. Pat. No. 4,677,797 of Hayes entitled "Clean Up Glove;" U.S. Pat. No. 4,768,818 of Kolic entitled "Disposable Litter Pick-Up Mitt;" U.S. Pat. No. 4,788,733 of Lerner entitled "Combined Cleaning Glove and Disposal Bag;" U.S. Pat. No. 4,902,283 of Rojko et al. entitled "Absorbable Cleaning Mitt for Wiping Babies;" U.S. Pat. No. 4,937,881 of Heise entitled "Garment Device of Handling and Storing Noxious Materials;" U.S. Pat. No. 4,964,188 of Olson entitled "Clean Up Device;" U.S. Pat. No. 5,020,159 of Hellickson entitled "Protective Article for Handling and Containing Waste Materials;" U.S. Pat. No. 5,020,160 of Cano entitled "Protective Disposable Hand Covering;" U.S. Pat. No. 5,149,159 of Bardes entitled "Disposable Collector and Container;" U.S. Pat. No. 5,210,880 of Yale entitled "Disposable Protective Outergloves;" and U.S. Pat. No. 5,301,806 of Olson entitled "Clean Up with Cut Resistant Layer."

An object of this invention is therefore to provide a device which enables an individual to remove a tampon from the individual's body and thereafter dispose of the tampon in a sanitary manner through a solid waste system rather than through a plumbing system, and a further object is to provide a compact item for such disposal. Other objects and advantages will become apparent from the following description and appended claims.

SUMMARY OF THE INVENTION

The present invention is directed to a device that satisfies the need for sanitary removal and disposal of a tampon. The device having the features of the present invention comprise a mitten having a front side and a back side adapted to fit over the hand and wrist of the individual. The mitten has an unitary finger portion, which includes a grasping portion attached near the area of the mitten covering the front (or palm-side) of the middle finger and an index finger portion which is detached from the unitary finger portion to approximately the mid-point of the index finger. The mitten further includes a thumb portion, a mid-section and a cuff portion, an absorbent pad affixed to the mid-section on the front (or palm-side) of the mitten, and an adhesive tab on the back side of the mitten. The grasping portion of the mitten provides a means for grasping a string attached to the tampon and is used to remove the tampon from a cavity of the wearer's body and to facilitate sanitary disposal of such tampon. When the mitten is inverted and rolled, the adhesive tab is adhered to the rolled mitten, thereby encasing the removed tampon within the mitten in a compact, disposable item for sanitary disposal with solid waste rather than by the plumbing system.

The mitten of the invention is preferably made of a relatively thin, highly flexible, impermeable, opaque, biodegradable material such as might be used in a surgical glove. The adhesive tab preferably comprises a peel-off protector which when removed exposes a pressure-sensitive adhesive on the adhesive tab. Other aspects and features of the invention will be more fully apparent from the following disclosure and appended claims.

BRIEF DESCRIPTION OF THE DRAWINGS

FIG. 1 shows a top plan view of the mitten of the invention.

FIG. 2 shows a side view of an individual utilizing the thumb and index finger portions of the mitten of the invention to initially gasp the string for removal of a tampon prior to removing the tampon from the individual's body cavity.

FIG. 3 is a view of the individual of FIG. 2 utilizing the grasping portion of the mitten to facilitate removal of the tampon from the individual's body cavity.

FIG. 4 is a close-up view of the mitten of FIG. 2 being utilized to initially grasp the removal string of the tampon.

FIG. 5 is a close-up view of the mitten of FIG. 3 showing the grasping portion of the mitten being utilized to remove the tampon from the individual's body cavity.

DETAILED DESCRIPTION OF THE INVENTION AND PREFERRED EMBODIMENTS THEREOF

Figure 12B:
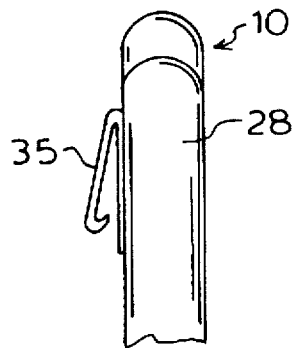
FIG. 12B is a partial side view of the portion of the mitten shown in FIG. 12A and illustrating its grasping portion in the alternative embodiment.

Referring now to the Figures, mitten 10 of the invention is adapted to fit over the hand and wrist of an individual I. Mitten 10 is used to remove a tampon 26 from the individual's body cavity, and package the tampon for easy and sanitary temporary storage and disposal as solid waste, rather than disposal through the plumbing system. Mitten 10 comprises unitary finger portion 12, partially detached index finger portion 28, thumb portion 14, mid-section 16, and cuff portion 18 as shown in FIG. 1. Unitary finger portion 12 includes in a first embodiment grasping portion 32, and in a second embodiment grasping portion 35 attached to the palm-side of the middle finger area close to the fingertip. Grasping portions 32 and 35 are each of an open ended V-shape and are each preferably formed of a molded plastic or plastic-coated metal, or other suitable material so as to have smooth edges and smooth outer surfaces to prevent trauma to the individual I during use. Both grasping portions provide smooth, spaced apart surfaces which extend inwardly in one direction to form an opening on unitary finger portion 12 and in the opposite direction extend to a location where the surfaces merge. Grasping portion 35 as best seen in FIG. 12B has a hook to assist in retaining the string. Unitary finger portion 12 minimizes the opportunity for leakage of fluids through the finger portion of the device during use, and also permits the entire mitten 10 to be easily inverted and rolled, unlike a glove-style device whose individual finger portions would be more prone to leak and would be more difficult to roll into a compact package. Partially detached index finger portion 28 enhances the individual I's grasping ability during removal of the tampon 26.

Mitten 10 is formed from a flexible, substantially impermeable, biodegradable, opaque material, such as the type of material used to form surgical gloves, so as to provide an invertible but protective covering for the individual's hand while minimally obstructing the sensitivity to the individual's fingers, which is essential to locating removal strong 30 of tampon 26. Mitten 10 is inverted to create a container for the tampon 26 following removal, and is rolled and secured to form a compact package for temporary storage and disposal. Thus, mitten 10 provides an item which is compact and easy to dispose, environmentally sound, and is capable of disguising the contents of the package for temporary storage and disposal. Mitten 10 is universally sized, or created in small, medium or large sizes. Mitten 10 can be formed to be worn on the right or left hand.

Mid-section 16 mounts an absorbent pad 20 made of a biodegradable material such as cotton for absorbing fluids during the removal and disposal process of tampon 26. Absorbent pad 20 terminates inwardly of the outer end of unitary finger portion 12 so that absorbent pad 20 does not obstruct the individual's fingers during use of mitten 10 and minimally obstructs sensitivity to the individual's fingers. Absorbent pad 20 is affixed to mitten 10 by an adhesive or any other suitable means.

Mitten 10 has adhesive tab 22 on the back side 40 of the outer extremity of cuff portion 18, as shown in FIG. 1. Adhesive tab 22 preferably comprises a pressure-sensitive adhesive which is covered with peel-off protector 24, which when removed from tab 22 exposes the pressure-sensitive adhesive on tab 22. The pressure-sensitive adhesive is selected from the various adhesives known in the art so as to be strong enough to secure the rolled mitten 10 for disposal. It has been found that one such adhesive tab and peel-off protector is sufficient for securing rolled mitten 10 for disposal.

Figure 11:
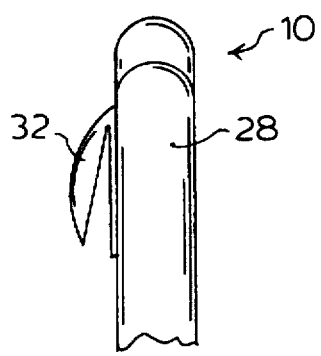
FIG. 11 is a partial side view of the mitten of FIG. 1 showing the grasping portion of the invention according to a first embodiment.

FIGS. 2 through 5 illustrate mitten 10 in use for removal of the tampon 26 from the individual I's body. The individual I puts mitten 10 over her hand. The individual I next utilizes the mitten 10 to grasp the removal string 30 of the tampon 26 being worn, as shown in FIGS. 2 and 4, with the thumb 14 and partially detached index finger 28 portions of the mitten 10. The individual I then utilizes the grasping portion 32 (FIG. 11) or 35 (FIG. 12B) of the mitten by hooking the removal string 30 of the tampon 26 through the opening of the grasping portion 32, in the manner shown in FIGS. 3 and 5. Subsequently, the individual I rotates her wrist while simultaneously pulling the string 30 of the tampon 26 to remove the tampon 26 from the individual I's body cavity by way of the grasping portion 32 or 35 of the mitten 10.

Figure 10:
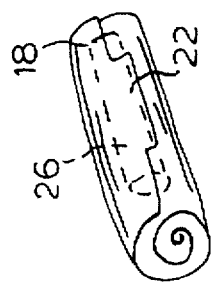
FIG. 10 is a view of the mitten of FIG. 7 which has been inverted, rolled and secured.
Figure 9:
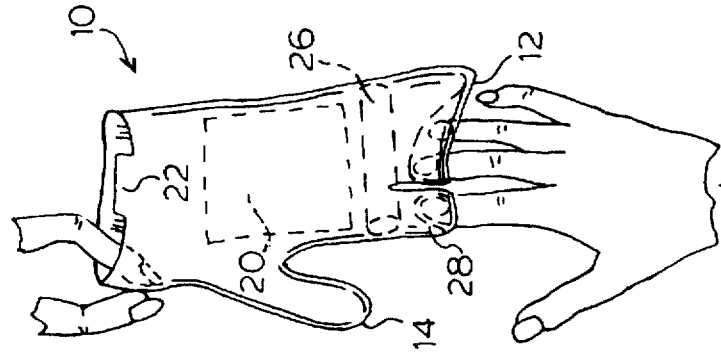
FIG. 9 is a view of the mitten of FIG. 7 showing the mitten almost completely removed from the individual's hand.
Figure 8:
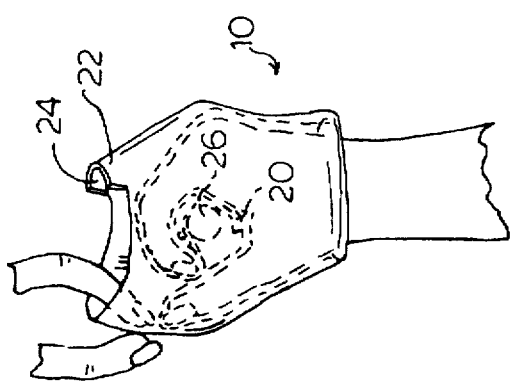
FIG. 8 is a view of the mitten of FIG. 7 showing the mitten being inverted around the individual's fist to encase the removed tampon.
Figure 7:
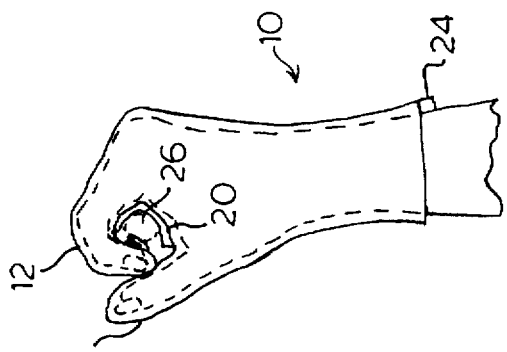
FIG. 7 is a view of the mitten of FIG. 1 showing the individual making a fist around the item for disposal.
Figure 6:
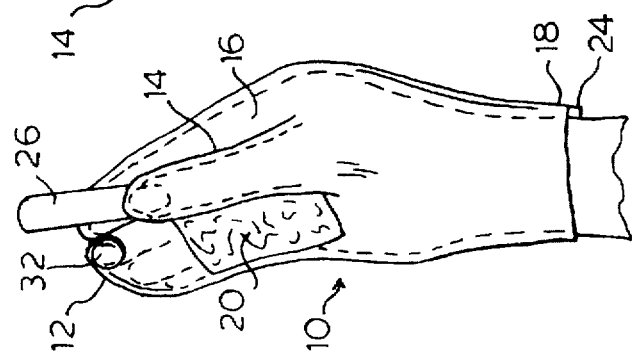
FIG. 6 is a view of the mitten of FIG. 1 worn by an individual and holding the item for disposal subsequent to removal.
Figure 12A:
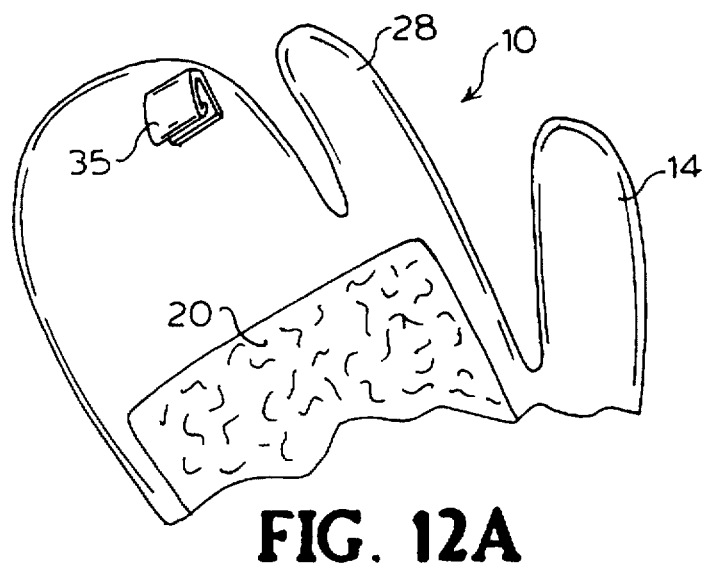
FIG. 12A is a top plan view of the outer portion of a mitten in an alternative embodiment of the invention according to a second embodiment.

FIGS. 6 through 10 illustrate mitten 10 in use for temporary storage and disposal of a tampon. The individual I puts mitten 10 on the individual's hand to remove tampon 26, as shown in FIG. 6. Subsequent to the removal of the tampon, the individual's hand makes a fist around tampon 26, as shown in FIG. 7. The individual I then grasps cuff 18 with the other hand, as shown in FIG. 8, to invert mitten 10 over the individual's fist and over tampon 26. While mitten 10 is removed from the individual's hand, it is inverted as seen in FIG. 8, to enclose the tampon 26. Inverted mitten 10 is then rolled and secured by removing peel-off protector 24 from tab 22 and adhering tab 22 to rolled and inverted mitten 10, as shown in FIG. 10, to form a compact item for disposal. Inverted, rolled and secured mitten 10 is then discarded with solid waste so that tampon 26 is not discarded through the plumbing system.

While the invention has been described with reference to specific embodiments thereof, it will be appreciated that numerous variations, modifications, and embodiments are possible and accordingly, all such variations, modifications, and embodiments are to be regarded as being within the spirit and scope of the invention.

I claim:

1. An invertible mitten serviceable prior to inversion as a device for removing a tampon of the type having a string attached thereto and after inversion being serviceable as a device for encasing the removed tampon and any string attached thereto within the mitten for sanitary disposal, comprising:
   a. a mitten formed of a relatively thin, highly flexible, impermeable, opaque material and adapted to fit over a selected hand and wrist of the wearer, said mitten having:
      (i) a front side;
      (ii) a back side;
      (iii) a unitary finger portion adapted to substantially enclose all but the thumb and a selected outer portion of the index finger of the wearer;
      (iv) a thumb portion integrally formed with said unitary finger portion and adapted to enclose the thumb of the wearer;
      (v) an index finger portion integrally formed with said unitary finger portion and adapted to enclose only a selected outer portion substantially equal to half the length of the index finger of the wearer, thereby enabling the enclosed said selected outer portion to move independently of said unitary finger portion;

(vi) a mid-section located outwardly of said unitary finger portion; and (vii) a cuff portion surrounding an opening into said mitten;

b. an absorbent pad affixed to said mid-section, on the front side of said mitten and inwardly of said index finger portion;

c. string grasping means secured to an outer extremity of said unitary finger portion on the said front side of said unitary finger portion and proximate said index finger portion and adapted to receive an outer end portion of the string attached to said tampon and effectively grasp said string such that when said mitten is worn by said wearer, and prior to its inversion, said tampon can be removed from a body cavity of the wearer by pulling on said string grasped by said means;

d. an adhesive tab mounted on said cuff portion, and having a peel-off protector which when removed exposes a pressure sensitive adhesive; and e. said mitten being further formed to permit said tampon after being removed from said body cavity to be grasped within said mitten adjacent said absorbent pad and held by the enclosed fingers of said wearer and the thinness and flexibility of the material forming said mitten permitting the entire said mitten including said unitary finger, thumb and index finger portion to be inverted and after inversion to permit said mitten to be rolled and said removed tampon and any string attached thereto encased within said inverted mitten and to be secured as a roll by attachment of said adhesive to a selected outer surface of said inverted mitten preparatory for disposal.

2. An invertible mitten as claimed in claim 1 wherein said string grasping means comprises a molded grasping means shaped in V-form with two opposing internal surfaces spaced apart and extending inwardly on said unitary finger portion and terminating in an opening for receiving said tampon string and in the opposite direction extending to a location where said surfaces merge.

3. An invertible mitten as claimed in claim 2 wherein said surfaces are smooth.

4. An invertible mitten as claimed in claim 3 wherein an outer one of said surfaces is formed with an inwardly extending hook adjacent said opening.

* * * * *

UNITED STATES PATENT AND TRADEMARK OFFICE
CERTIFICATE OF CORRECTION

PATENT NO. : 5,740,554
DATED : April 21, 1998
INVENTOR(S) : B. Bernetiae Reed

It is certified that error appears in the above-identified patent and that said Letters Patent is hereby corrected as shown below:

Column 1, line 46, "4,677,797" should read --4,677,697--.

Column 1, line 60, "Outergloves" should read --Overgloves--.

Column 3, line 47, "strong" should read --string--.

Column 5, line 13, "said" second appearance should be eliminated.

Column 5, line 20, before "means" insert --grasping--.

Signed and Sealed this

Fourteenth Day of July, 1998

Attest:

BRUCE LEHMAN

*Attesting Officer*  *Commissioner of Patents and Trademarks*